United States Patent
Sorgato et al.

(10) Patent No.: US 10,107,745 B2
(45) Date of Patent: Oct. 23, 2018

(54) METHOD AND DEVICE FOR ESTIMATING OPTICAL PROPERTIES OF A SAMPLE

(71) Applicants: Commissariat à l'énergie atomique et aux énergies alternatives, Paris (FR); Centre National De la Recherche Scientifique, Paris (FR)

(72) Inventors: Veronica Sorgato, Quito (EC); Michel Berger, Claix (FR); Anne Planat-Chretien, St Egreve (FR); Christine Vever-Bizet, Paris (FR); Genevieve Bourg-Heckly, Paris (FR); Charlotte Emain, Izeaux (FR)

(73) Assignees: Commissariat à l'énergie atomique et aux énergies alternatives, Paris (FR); Centre National De la Recherche Scientifique, Paris (FR); Université Pierre et Marie Curie (Paris 6), Paris (FR)

( * ) Notice: Subject to any disclaimer, the term of this patent is extended or adjusted under 35 U.S.C. 154(b) by 0 days.

(21) Appl. No.: 15/493,589

(22) Filed: Apr. 21, 2017

(65) Prior Publication Data
US 2017/0307524 A1    Oct. 26, 2017

(30) Foreign Application Priority Data
Apr. 22, 2016    (FR) .................... 16 53587

(51) Int. Cl.
*G01N 21/55* (2014.01)
*G01N 21/47* (2006.01)
*G01N 33/483* (2006.01)

(52) U.S. Cl.
CPC ....... *G01N 21/474* (2013.01); *G01N 33/4833* (2013.01); *G01N 2021/4742* (2013.01); *G01N 2201/088* (2013.01)

(58) Field of Classification Search
CPC ........ G01N 21/47; G01N 21/49; G01N 21/64; G01N 21/65; G01N 21/474;
(Continued)

(56) References Cited

U.S. PATENT DOCUMENTS

| 7,480,042 B1* | 1/2009 | Phillips ................ G01N 21/278 356/243.1 |
| 2014/0241994 A1* | 8/2014 | Koenig ................ A61B 5/0075 424/9.8 |
| 2016/0231249 A1* | 8/2016 | Roig ................. G01N 21/6486 |

FOREIGN PATENT DOCUMENTS

EP    2 762 064 A2    8/2014

OTHER PUBLICATIONS

French Preliminary Search Report dated Feb. 14, 2017 in French Application 16 53587 filed on Apr. 22, 2016 (with English Translation of Categories of Cited Documents and Written Opinion).
(Continued)

*Primary Examiner* — Jamil Ahmed
(74) *Attorney, Agent, or Firm* — Oblon, McClelland, Maier & Neustadt, L.L.P.

(57) ABSTRACT

A method and a device allow optical properties of a sample to be estimated. The method includes the illumination of the sample by a first light source, and the formation of an image of the sample thus illuminated, on the basis of which a first optical property is estimated, at various points on a surface of the sample. The method also includes measuring an auxiliary optical property of the sample and estimating the first optical property, taking account of the auxiliary optical property measured on the sample.

14 Claims, 6 Drawing Sheets

(58) Field of Classification Search
CPC ............ G01N 21/6486; G01N 33/483; G01N 33/4833; G01N 2021/4742; G01N 2201/088; G01J 1/10; A61K 49/00; G06F 19/00
See application file for complete search history.

(56) References Cited

OTHER PUBLICATIONS

Brandon S. Nichols et al. "A Quantitative Diffuse Reflectance Imaging (QDRI) System for Comprehensive Surveillance of the Morphological Landscape in Breast Tumor Margins," PLOS ONE, DOI:10.1371/journal.pone.0127525, Jun. 2015, pp. 25.

Sulochana Dhar et al. "A diffuse reflectance spectral imaging system for tumor margin assessment using custom annular photodiode arrays," Biomedical Optics Express 3213, vol. 3, No. 12, Dec. 2012, pp. 12.

Brandon S. Nichols et al. "Performance of a lookup table-based approach for measuring tissue optical properties with diffuse optical spectroscopy," Journal of Biomedical Optics 17(5), 057001, May 2012, pp. 9.

Asgeir Bjorgan et al. "Estimation of skin optical parameters for real-time hyperspectral imaging applications", J. Biomed. Opt. 19(6), 066003, Jun. 2014, pp. 12.

Veronica Sorgato et al. "Non-contact Quantitative Diffuse Reflectance Spectroscopy," Proceedings of SPIE vol. 9538, 95380U, 2015, pp. 8.

Chung-Chieh Yu et al. "Quantitative spectroscopic imaging for non-invasive early cancer detection," Optics Express 16227, vol. 16, No. 20, Sep. 2008, pp. 13.

\* cited by examiner

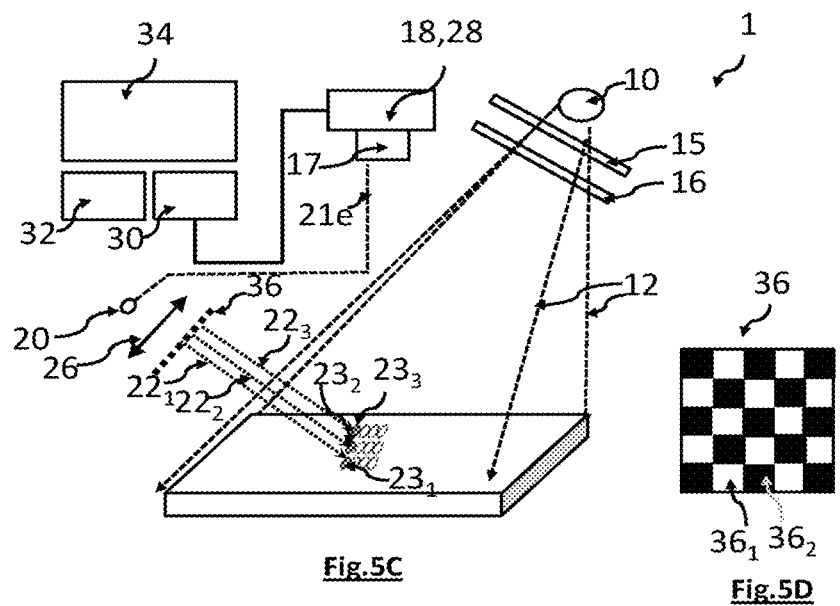
Fig.5C
Fig.5D
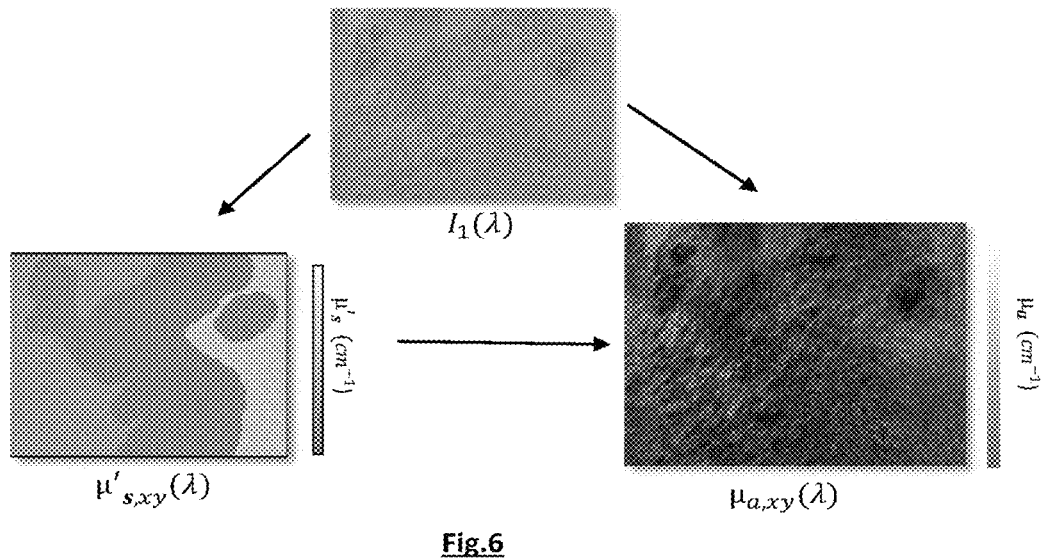
Fig.6

METHOD AND DEVICE FOR ESTIMATING OPTICAL PROPERTIES OF A SAMPLE

FIELD OF THE INVENTION

The field of the invention is that of the characterization of optical properties of a sample, for example a skin sample.

BACKGROUND

Optical measurements making it possible to characterize optical properties of samples are widespread. Measurements based on the detection of a signal backscattered or reflected by a sample illuminated by a light beam may be cited in particular. These may entail, for example, Raman spectrometry, fluorescence imaging or diffuse reflectance spectrometry.

Diffuse reflectance spectrometry, commonly referred to by the acronym DRS, consists in utilizing the light backscattered by a scattering object subjected to pointlike illumination. This technique is described in document EP2762064 and in publication Sorgato V. "Non-contact quantitative diffuse reflectance spectroscopy", Proceedings of SPIE Vol. 9538, 95380U (2015), referred to hereinafter as "Sorgato 2015". These documents describe a probe including a central optical fibre, connected to a light source and intended to direct a thin beam of light onto a sample, in particular a skin sample. Optical fibres positioned around the central optical fibre, termed detection fibres, collect optical radiation backscattered by the sample. Means for spectrally analysing the backscattered radiation allow optical properties of the sample to be estimated, in particular optical properties relating to scattering and to absorption. The probe may be brought into contact with or remote from the sample to be characterized. This technique makes it possible to quantitatively characterize these optical properties, but it is a local characterization. The optical properties are determined within an elementary volume of the sample, this elementary volume being dependent on the geometry of the probe.

It is possible to take DRS measurements at various discrete positions on a sample, according to a spatial mesh, so as to obtain a two-dimensional characterization of the optical properties of the sample. Such an approach is presented in publication Nichols B S et al. "A Quantitative Diffuse Reflectance Imaging (QDRI) System for Comprehensive Surveillance of the Morphological Landscape in Breast Tumor Margins", PLoS ONE 10, 2015, referred to hereinafter as "Nichols 2015". The device and method described in this publication make it possible to characterize optical properties according to a discrete two-dimensional mesh comprising 49 points distributed regularly in a matrix arrangement.

As an alternative to DRS, multispectral imaging, referred to by the acronym MSI, makes it possible to characterize an optical property of a sample in two dimensions. Publication Bjorgan A, "Estimation of skin optical parameters for real-time hyperspectral imaging applications", J. Biomed. Opt. 19(6), 066003, Jun. 4, 2014, referred to hereinafter as "Bjorgan 2014", is one example thereof. This publication describes the use of images of a sample, formed in various spectral bands, in order to evaluate a two-dimensional spatial distribution of the absorption coefficient of the sample, this being done in the various spectral bands. The evaluation is based on a value of the reduced absorption coefficient that is determined beforehand on the basis of data that are available in the literature. Since it is based on images, this method may be applied across a wide field of observation, and provides both good spatial and spectral resolution. However, as described below, the inventors have demonstrated that such a method may result in a substantial measurement error when it is sought to obtain a precise quantification of the absorption coefficient.

The inventors have sought a method making it possible to quantitatively characterize the scattering and absorption optical properties of a sample, providing an extended field of observation, so as to quickly obtain a two-dimensional spatial distribution of these optical properties. This method implements simple and inexpensive devices and is robust enough to be applied outside a research laboratory, for example in an operating theatre or in an analytical laboratory.

SUMMARY

One subject of the invention is a method for estimating optical properties of a sample, including the following steps:
a) illuminating the surface of the sample using a first light beam, produced by a first light source;
b) acquiring, using a first image sensor, a first image of light radiation backscattered by the sample thus illuminated;
c) using the first image, determining, at multiple regions of interest on the surface of the sample, a first quantity of interest, representative of a quantity of the light radiation backscattered by the sample;
d) estimating a first optical property at each of the regions of interest, using the first quantity of interest;
the method including, prior to step d), a step of measuring an optical property, referred to as the auxiliary optical property, of the sample, that differs from the first optical property, each estimate made in step d) taking account of the auxiliary optical property thus measured on the sample.

In step c) a quantity of interest may be obtained for each region of interest.

Thus, the auxiliary optical property measured on the sample is used to determine the first optical property of the sample.

The first light beam is emitted by the first light source in a first spectral band. Preferably, the first optical property and the auxiliary optical property are determined in one and the same spectral band.

According to a preferred embodiment, the first optical property is a light absorption property of the sample, the auxiliary optical property being a light scattering property of the sample; According to another embodiment, the first optical property is a light scattering property of the sample, the auxiliary optical property being a light absorption property of the sample.

According to one embodiment, the step of measuring the auxiliary optical property includes the following sub-steps:
i) illuminating the surface of the sample using an auxiliary light beam, produced by an auxiliary light source, so as to form, on the surface of the sample, an elementary illumination zone, corresponding to the portion of the surface illuminated by the auxiliary light beam;
ii) measuring, using an auxiliary photodetector, a backscattering signal, representative of radiation backscattered by the sample, the backscattered radiation emanating from an elementary backscattering zone, separated from the elementary illumination zone and located at a distance, referred to as the backscattering distance, from the latter;

iii) estimating the auxiliary optical property of the sample on the basis of the backscattering signal measured in sub-step ii).

The auxiliary light beam can be emitted by the auxiliary light source in a second spectral band. The first spectral band and the second spectral band may overlap or may be merged.

Sub-step ii) may include obtaining, on the basis of the backscattering signal, a quantity of interest, referred to as the auxiliary quantity of interest, representative of a quantity of the radiation backscattered by the sample, at a backscattering distance, subsequent to its illumination by the auxiliary light beam. Sub-step iii) may include comparing the auxiliary quantity of interest with a plurality of estimates of this auxiliary quantity of interest, each estimate being made by considering a predetermined value of the auxiliary quantity of interest. Preferably, sub-step ii) is carried out by considering various backscattering distances, step iii) taking account of the respective backscattering signals measured at each of these backscattering distances.

According to one embodiment, in sub-step i), the sample is successively or simultaneously illuminated by a plurality of auxiliary light beams so as to form, on the surface of the sample, a plurality of elementary illumination zones that are spaced apart from one another; sub-steps ii) and iii) are then implemented by considering a backscattered signal emitted at at least one backscattering distance from each elementary illumination zone, so as to estimate the auxiliary optical property in as many surface elements as there are auxiliary light beams.

According to one embodiment, step d) includes comparing the first quantity of interest determined in step c) with a plurality of estimates of this quantity of interest, each estimate being made by considering a predetermined value of the first optical property and by taking account of the auxiliary optical property previously measured on the sample. The first optical property may in particular be obtained by determining the optical property that minimizes the comparison.

According to one embodiment, step c) includes segmenting the first image into various regions of interest, a first quantity of interest being determined at each region of interest. The segmentation may be carried out according to the intensity of pixels of the image, or based on an a priori estimate of the composition of the sample at each region of interest. Each region of interest in the image is optically coupled to one region of interest on the surface of the sample. A region of interest in the image may comprise one pixel or a plurality of pixels of said image. Step c) may comprise the following sub-steps:
  ci) determining an intensity that is representative of each region of interest in the first image;
  cii) applying a first calibration factor to said intensity that is representative of each region of interest, so as to obtain said first quantity of interest.

The first calibration factor may be obtained on the basis of a calibration sample the optical properties of which are known. It may represent a ratio of a quantity of radiation backscattered by said calibration sample, this quantity being modelled, to an intensity measured by putting said calibration sample in the place of the sample under examination.

According to one embodiment, steps c) and d) are implemented iteratively by considering, in the first iteration, a first calibration factor corresponding to an arbitrarily chosen calibration sample. During a subsequent iteration, in step c), the first quantity of interest is determined by applying a first calibration factor corresponding to the first optical property estimated in step d) of a preceding iteration.

The first calibration factor may also be chosen so as to correspond to the auxiliary property measured on the sample.

According to one embodiment, the auxiliary optical property of the sample may be measured at a plurality of surface elements of the sample. The method may then include interpolating said auxiliary optical property on the basis of at least two auxiliary optical properties measured beforehand, so as to establish a spatial, in particular two-dimensional, distribution of said auxiliary optical property.

According to one embodiment, the method includes:
  determining at least one surface element of the sample on the basis of the first image acquired in step b);
  measuring an optical property, referred to as the auxiliary optical property of the sample, that differs from said first optical property, the auxiliary optical property of the sample being measured according to each surface element thus determined.

Another subject of the invention is a device for estimating optical properties of a sample including:
  a first light source, capable of emitting a first light beam that is propagated in the direction of the sample;
  a first image sensor, capable of acquiring a first image of first light radiation backscattered by the sample;
  an auxiliary light source, capable of emitting an auxiliary light beam that is propagated in the direction of the sample, so as to form, on the surface of the latter, an elementary illumination zone, corresponding to the portion of a surface of the sample that is illuminated by the auxiliary light beam;
  an auxiliary photodetector capable of measuring radiation backscattered by the sample, at a backscattering distance from the elementary illumination zone, subsequent to the illumination of the sample by the auxiliary light source;
  a microprocessor, configured to determine an auxiliary optical property of the sample on the basis of the backscattered radiation measured by the auxiliary photodetector, the microprocessor also being configured to determine a first optical property differing from the auxiliary optical property, at various points on the surface of the sample, each point being determined on the basis of the first image acquired by the first image sensor, the auxiliary optical property being determined by taking account of the auxiliary optical property.

The auxiliary photodetector may in particular be an image sensor. It may be the first image sensor.

According to one embodiment, the auxiliary light source is capable of simultaneously forming a plurality of elementary illumination zones, spaced apart from one another, on the surface of the sample. The device may include a mask, interposed between the auxiliary light source and the sample, the mask including transparent portions, allowing the auxiliary light beam to pass through, and opaque portions, blocking the auxiliary light beam, such that each elementary illumination zone is formed by a projection of a transparent portion onto the surface of the sample Another subject of the invention is a method for estimating optical properties of a sample, including the following steps:
  1) illuminating the surface of the sample using a first light beam, produced by a first light source;
  2) acquiring, using a first image sensor, a first image of light radiation backscattered by the sample thus illuminated;
  3) selecting a region of interest in the first image;

4) determining a plurality of first calibration factors, each first calibration factor taking the form of a ratio of:
   a model of a quantity of radiation backscattered by the calibration sample the first optical property of which is known;
   to an intensity representative of a calibration image acquired by the first image sensor when a calibration sample is illuminated by the first light source,
   such that a plurality of calibration factors corresponding to respective calibration samples having first optical properties of various values is available, each first calibration factor being associated with one value of the first optical property;
5) determining a first quantity of interest, representative of a quantity of radiation backscattered by the sample, in the region of interest by multiplying an intensity that is representative of the region of interest by a first calibration factor;
6) estimating a first optical property at various regions of interest on the surface of the sample, using the first quantity of interest thus determined;
7) reiterating steps 5) and 6) by considering, in step 5), a first calibration factor corresponding to the value of the first optical property estimated in step 6) of the preceding iteration, the reiteration being carried out until a convergence criterion is reached.

According to this embodiment, steps 3) to 7) may be carried out for various regions of interest in the first image, each region of interest in the image being optically coupled to a region of interest on the surface of the sample.

According to one embodiment, the method comprises measuring an auxiliary optical property, such as defined above, on one or more surface elements of the sample. In step 5), the first quantity of interest may be determined by considering a first calibration factor corresponding to the auxiliary optical property.

The term "first calibration factor corresponding to an optical property" is understood to mean a first calibration factor that is representative of a calibration sample having the optical property. Such a calibration factor may be measured or interpolated on the basis of measured calibration factors.

Other advantages and features will become more clearly apparent from the following description of particular embodiments of the invention, which are provided by way of non-limiting examples, and which are shown in the figures listed below.

BRIEF DESCRIPTION OF THE DRAWINGS

FIGS. 5B and 5C respectively schematically show two different embodiments of a device according to the invention. FIG. 5D shows a mask that may be applied in the embodiment disclosed in FIG. 5C.

FIG. 6 shows three images that may be obtained by implementing the invention.

DETAILED DESCRIPTION OF THE ILLUSTRATED EMBODIMENTS

Figure 1:
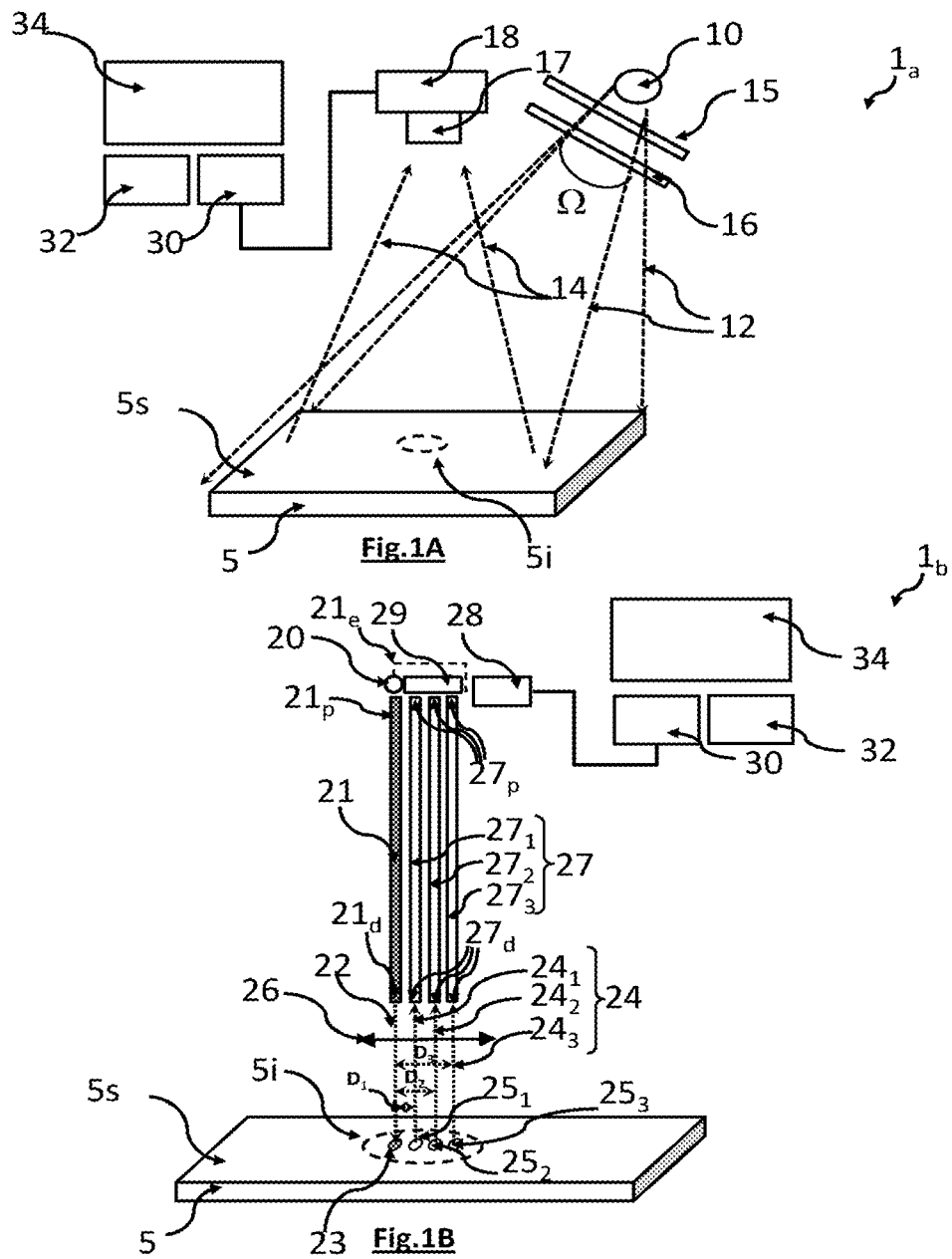
FIG. 1A shows a first component of a device according to the invention for estimating an optical property of a sample on the basis of a first image, according to a first modality.
FIG. 1B shows a second component of a device according to the invention for estimating an auxiliary optical property of a sample, according to a second modality.

FIG. 1A shows a first component 1a of a device 1 allowing an image of a sample to be formed and an optical property, or a spatial distribution of such an optical property, to be deduced therefrom.

The term "optical property" refers to a property governing the absorption or scattering of light in the sample. It may be an optical property relating to absorption, for example the absorption coefficient $\mu_a$, or an optical property relating to scattering, for example a reduced scattering coefficient $\mu_s'$, a scattering coefficient $\mu_s$ or a scattering anisotropy coefficient. These coefficients are known to those skilled in the art.

The first component 1a allows a first modality, referred to as a scattering spectral imaging modality, to be applied to the sample. In general, according to this first modality, the sample 5 is illuminated by a first light source 10 and a first image $I_1(\lambda)$ of this sample is formed using a first image sensor 18. The light source may be a white light source, in which case the first image sensor 18 is spectrally resolved, allowing images of the sample to be acquired in various spectral bands λ. The term "spectral band" is understood to mean a wavelength or a range of wavelengths.

Alternatively, the first light source 10 may emit a first light beam 12, incident to the sample, in succession in various spectral bands λ, in which case the first image sensor 18 acquires as many images of the sample as there are spectral bands.

In the example shown, the first light source 10 is a white light source associated with a filter wheel 15, the latter including a plurality of filters the passband of which defines the spectral band λ of the first light beam 12, emitted by the source and which is propagated to the sample 5. The first light source 10 may be coupled to a scatterer 16, allowing a solid angle Ω of illumination of the sample 5 to be increased. Preferably, a substantial portion of the surface 5s of the sample is illuminated by the first light beam 12, the area of the illuminated surface preferably being larger than 4 cm², or even larger than 10 cm'. This surface 5s is typically of the order of 100 cm².

Under the effect of the illumination provided by the first light beam 12, the sample backscatters radiation 14, referred to as first backscattered radiation, this radiation being detected by the first image sensor 18 through an objective 17.

The device also includes a processor 30, for example a microprocessor, linked to a memory 32 and capable of executing instructions stored in the memory, so as to implement certain steps of the method described below. The processor may be linked to a screen 34. The processor 30 carries out said steps on the basis of the first images acquired by the image sensor 18 and/or on the basis of backscattering signals detected by an auxiliary photodetector 28 described in conjunction with FIG. 1B.

Figure 2:
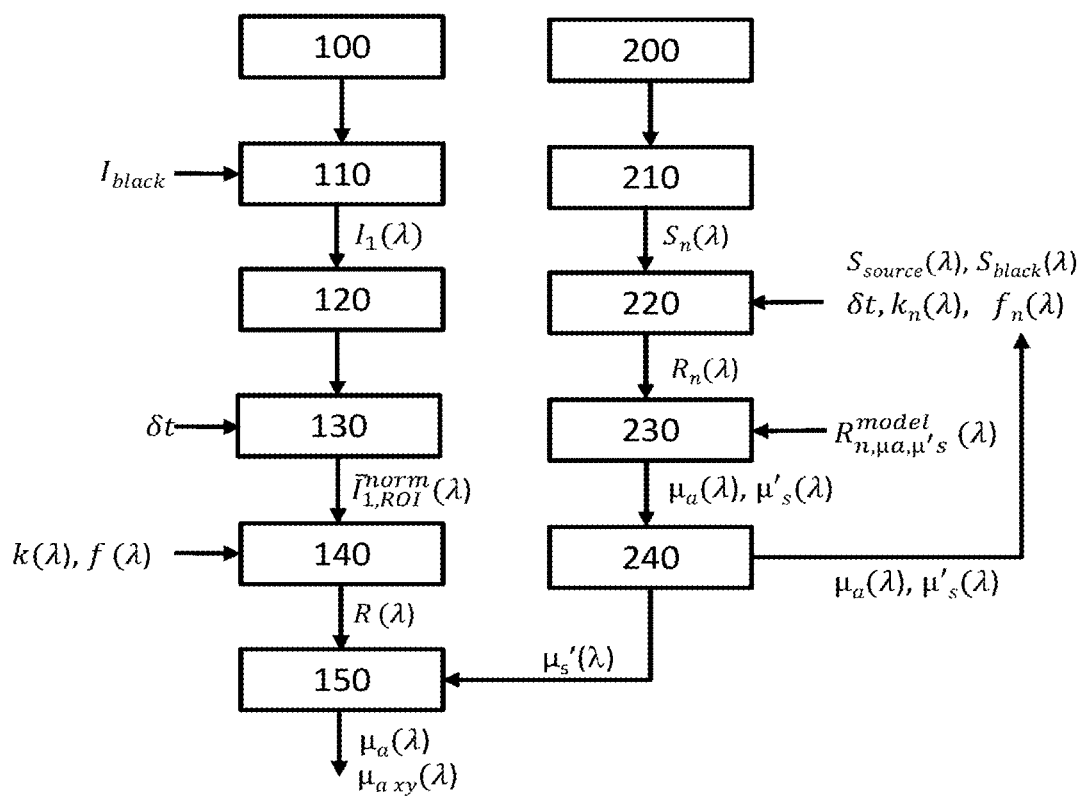
FIG. 2 illustrates the steps of a method according to the invention.

On the basis of each first image $I_1(\lambda)$ acquired by the image sensor 18 in a spectral band $\lambda$, optical properties of the sample 5 may be estimated in the spectral band, as described below in conjunction with FIG. 2.

FIG. 1B shows a second component 1b of the device 1 making it possible to implement the invention according to a second modality, referred to as a diffuse reflectance spectrometry (DRS) modality. As described in the documents relating to DRS cited in the prior art, an auxiliary light source 20, for example a white light source, is coupled to an optical fibre 21, referred to as the illumination optical fibre, so as to form an auxiliary light beam 22 that is propagated in the direction of the sample 5. The illumination optical fibre extends between a proximal end $21_p$ positioned facing the auxiliary light source 20, collecting the light emitted thereby, and a distal end $21_d$ positioned facing the sample 5. The distal end $21_d$ may be brought into contact with the sample 5 or be kept at a distance from the sample 5, as shown in FIG. 1B. In the latter case, an optical system 26, for example an objective or a lens, allows the auxiliary light beam 22 to be focused on the surface 5s of the sample. The optical system 26 may have a magnification factor that is higher or lower than 1. In the example shown, the magnification factor is equal to 1.

The auxiliary light beam 22 forms, on the surface 5s of the sample, an elementary illumination zone 23 that corresponds to the intersection of the auxiliary light beam 22 with the surface 5s. The term "elementary zone" refers to a zone of defined shape and including one dimension that is smaller than or equal to 1 cm, and preferably smaller than or equal to 1 mm. The term "dimension" is understood to mean a diameter, a diagonal or a width. The area of such an elementary zone is preferably smaller than 1 $cm^2$, or even smaller than 1 $mm^2$. In the example shown in FIG. 1B, the elementary illumination zone 23 is located in an image focal plane of the optical system 26, while the distal end $21_d$ of the illumination optical fibre 21 is located in the object focal plane of this optical system. The diameter of the illumination optical fibre 21 is generally between 50 μm and 1 mm, and is for example equal to 500 μm.

The device includes a plurality of detection optical fibres 27, each extending between a distal end $27_d$, facing the sample, and a proximal end $27_p$. Each detection fibre 27 is capable of collecting radiation 24, referred to as second backscattered radiation, backscattered by the sample 5 when the sample is illuminated by the auxiliary light beam 22. The distal ends $27_d$ of each detection fibre 27 are positioned at different distances from the distal end $21_d$ of the illumination fibre 21, so that each detection fibre is capable of collecting radiation backscattered by the sample, emanating from the surface of the sample at a distance $D_n$ from the illumination zone 23, referred to as the backscattering distance, which differs from one to the other.

The principle of this modality is to determine a quantity of photons backscattered by the sample over one, or preferably multiple, backscattering distances $D_n$. To achieve this, each detection optical fibre 27 collects backscattered radiation 24 emanating from an elementary detection zone 25, this zone extending to a backscattering distance $D_n$ from the elementary illumination zone 23. The auxiliary photodetector 28 detects a backscattered signal $S_n$, the intensity of which depends on a quantity of photons backscattered to the backscattering distance $D_n$.

In FIG. 1B, three detection fibres 27 are shown:
A first detection fibre $27_1$, capable of collecting scattering radiation $24_1$ emanating from the surface of the sample at an elementary detection zone $25_1$ extending to a first backscattering distance $D_1$ with respect to the elementary illumination zone 23.
A second detection fibre $27_2$, capable of collecting scattering radiation $24_2$ emanating from the surface of the sample at an elementary detection zone $25_2$ extending to a second backscattering distance $D_2$ with respect to the elementary illumination zone 23.
A third detection fibre $27_3$, capable of collecting scattering radiation $24_3$ emanating from the surface of the sample at an elementary detection zone $25_3$ extending to a third backscattering distance $D_3$ with respect to the elementary illumination zone 23.

The first, second and third backscattering distances are non-zero and differ from one another. Depending on the magnification factor of the optical system 26, they may extend from a few tens of lam to a few mm, or even cm, from the elementary illumination zone 23. The elementary backscattering zones 25 are preferably separated from the elementary illumination zone 23, the term "separated" meaning that there is no intersection between an elementary backscattering zone 25 and the elementary illumination zone 23.

Multiple detection optical fibres may be combined at elementary detection zones extending to one and the same backscattering distance from the elementary illumination zone. In this case, these fibres may be positioned in a circle around the elementary illumination zone. This makes it possible to increase the quantity of backscattering radiation detected, corresponding to one and the same backscattering distance. The sensitivity of the measurement is thus enhanced. This also makes it possible to obtain a mean of the backscattered radiation at each backscattering distance. Such configurations, referred to as concentric configurations, are described in document EP2762064 or in publication "Sorgato 2015" cited above.

The proximal end $27_p$ of each detection optical fibre is coupled to an optical switch 29, allowing selective coupling of each optical fibre to an auxiliary photodetector 28, this photodetector being, in this example, a spectrophotometer. The spectrophotometer is capable of forming a wavelength spectrum of each radiation backscattered over a backscattering distance. The processor 30 is capable of processing the spectra so as to estimate an auxiliary optical property of the sample, as explained in conjunction with FIG. 2.

A notable difference between the first component 1a of the device, shown in FIG. 1A, and the second component 1b of the device, shown in FIG. 1B, relates to the spatial extensions of the first light beam 12 and of the auxiliary light beam 22. As mentioned above, the surface of the sample illuminated by the first light beam 12 is larger than a few $cm^2$, and most often larger than 5 $cm^2$, or even 10 or 100 $cm^2$, while the surface of the sample illuminated by the auxiliary light beam 22 is smaller than 1 $cm^2$. The first modality makes it possible to simultaneously determine an optical property over a large area of the sample, i.e. over various regions of interest on the surface 5s of the sample, while the second modality makes it possible to quantitatively measure a local optical property of the sample. Thus, the first modality make it possible to obtain, on the basis of one and the same image $I_1(\lambda)$, a two-dimensional spatial distribution of an optical property, which is not possible with the second modality unless the number of illumination optical fibres and detection optical fibres is multiplied, as described in publication "Nichols 2015" cited above.

The main steps of a method for determining optical properties of a sample will now be described, in conjunction with FIG. 2. Steps 100 to 150 relate to the first modality, in this instance scattering spectral imaging, while steps 200 to 240 relate to the second modality, in this instance diffuse reflectance spectrometry.

Step 100: illumination of the sample by means of the first light source.

In this step, the sample is illuminated by means of the white light source 10, emitting a first light beam 12 that is propagated to the sample in a spectral band $\lambda$ that is adjusted by the filter wheel 15. In this example, the light source used is a Schott halogen source with the reference KL 2500 LCD. It is combined with a filter wheel 15 including three filters defining spectral bands $\lambda$ that are centred on the 500 nm, 600 nm et 700 nm wavelengths, respectively. The bandwidth of each filter, corresponding to the width at half maximum of the emission peak, is of around 10 nm. The scatterer 16 is a ring at which light guides arising from the first light source 10 terminate. This allows the light to be distributed, as uniformly as possible, over a solid angle of emission $\Omega$.

Steps 110 and 150 below are described with reference to one spectral band $\lambda$, but they may be implemented in succession in each spectral band of the first beam 12 that is emitted by the first light source and reaches the sample.

Step 110: Acquisition of an image.

Figure 3A:
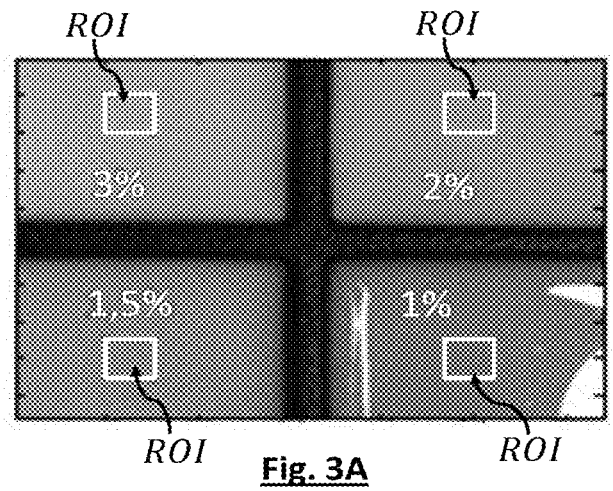
FIG. 3A shows an image of test samples obtained using the configuration shown in FIG. 1A.

The first image sensor acquires a first image $I_1(\lambda)$ of radiation 14 formed by backscattering, by the sample 5 of the first light beam 12, at a wavelength or in a spectral band $\lambda$. FIG. 3A shows such an image, the sample being formed from various test samples having different optical scattering properties and described in conjunction with FIGS. 4A to 4D.

The acquired image $I_1(\lambda)$ is preferably corrected from a dark image $I_{black}$, obtained in the dark over one and the same duration of acquisition, the first light source being switched off. The dark image $I_{black}$ is representative of the noise of the first image sensor and of a darkness level of the device. It is also preferably normalized by a "white" image $I_{flatfield}$, also referred to by the term "flat field", which is intended to correct spatial heterogeneities in the illumination of the sample and the detection efficiency of the image. The illumination of the sample by the first light source 10 might indeed not be uniform. Moreover, especially due to optical components in the objective 17, the detection efficiency is not uniform, in particular because of vignetting effects at the periphery of the image. The acquired image is normalized by the flat field image $I_{flatfield}$, this image being obtained by producing an image of a sample the backscattering of which is considered to be uniform, and by normalizing the image thus obtained using the intensity value of the most intense pixel of the image. It is common practice to make use of such a flat field image.

Step 120: Segmenting the first image into regions of interest and selecting a region of interest.

In this step, one or more regions of interest ROI are selected in the first image $I_1(\lambda)$ obtained in step 110. A region of interest ROI may correspond to various adjacent pixels of the first image $I_1(\lambda)$ having one and the same intensity level, or a comparable intensity level. Each region of interest in the first image is associated with a region of interest on the sample, to which it is coupled by means of the objective 17. In the image of FIG. 3A, 4 regions of interest ROI are shown, each being defined by a rectangle. Each region of interest corresponds to a test sample described in conjunction with FIGS. 4A to 4D. Such a selection allows artefacts, in particular artefacts due to specular reflection, to be avoided. A region of interest may comprise only one pixel. It may also group together pixels that are not adjacent but have one and the same intensity or a comparable intensity on the first image $I_1(\lambda)$.

A region of interest may also correspond to a region of the sample in which it is considered, either arbitrarily or on the basis of prior measurements, that an optical property of the sample is uniform, or that a composition of the sample is uniform.

Step 130: Determining a mean intensity in each region of interest.

In this step, a quantity of interest representative of each region of interest is determined. If $I_{1,ROI}(\lambda)$ denotes the image of the region of interest ROI, a mean of the intensity of the pixels in this region of interest is calculated, so as to obtain a mean intensity $\bar{I}_{1,ROI}(\lambda)$.

This mean intensity may be normalized by a duration of acquisition $\delta t$ of the image, such that $$\bar{I}_{1,ROI}^{norm}(\lambda) = \frac{\bar{I}_{1,ROI}(\lambda)}{\delta t}, \qquad (1)$$

the exponent norm denoting the fact that the image is normalized by the duration of acquisition.

Step 140: Taking account of corrective factors.

This step consists in applying a calibration factor $f(\lambda)$, referred to as the first calibration factor, to the mean intensity. This first calibration factor takes account of the intensity of the first light beam 12 that is incident on the sample, as well as the sensitivity of the first image sensor 18. It is determined in a calibration phase, implementing a calibration sample, or calibration phantom, the optical properties of which are known. The first calibration factor $f(\lambda)$ corresponds to a ratio of a modelled reflectance $R_{calib}^{model}(\lambda)$ of the calibration sample to the mean intensity of an image $\bar{I}_{calib}^{norm}(\lambda)$ of the sample acquired by the device, while keeping the same experimental parameters as in the analysis of the sample: the same adjustments to the light source 10 and the image sensor 18, the same distance from the calibration sample with respect to the source and to the image sensor and the same level of darkness in which the sample is placed.

The first calibration factor is such that $$f(\lambda) = \frac{R_{calib}^{model}(\lambda)}{\bar{I}_{calib}^{norm}(\lambda)}. \qquad (2)$$

Furthermore, certain parameters of the device may vary between the time $t_0$ at which the calibration described above was carried out and the time $t$ of measurement on the sample under examination. For example, this could be the variation in the intensity of the light source or in the response of the light guides, or a variation in the sensitivity of the image sensor and, more generally, in various components of the device. In order to take account of this variability, a first correction factor $k(\lambda)$ is applied, such that $$k(\lambda) = \frac{I_{t\text{-}ref}(\lambda)}{I_{t0\text{-}ref(\lambda)}}, \quad (3)$$

where $I_{t\text{-}ref}(\lambda)$ and $I_{t0\text{-}ref(\lambda)}$ denote an intensity, measured by the image sensor 18, of a reference phantom at the time of measurement t and at an initial time $t_0$, respectively. The reference phantom may be a calibration sample or a phantom including a surface the reflectance of which is constant. For example, it may be a disc applied to a support that is positioned facing the image sensor 18 before the measurements are taken. The measurements of the reference phantom, at the initial time $t_0$ and at the measurement time t, are taken according to the same experimental parameters.

The application of the first calibration factor $f(\lambda)$ and of the first correction factor $k(\lambda)$ makes it possible to obtain a reflectance $R(\lambda)$ of the analysed sample 5, such that:

$$R(\lambda) = \bar{I}_{1,ROI}{}^{norm}(\lambda) \times k(\lambda) \times f(\lambda) \quad (4).$$

Thus, on the basis on the first image, a first quantity of interest $R(\lambda)$ representative of the reflectance of the sample 5 in the region of interest ROI in question is obtained, this reflectance representing a quantity of radiation 14 backscattered by the region of interest normalized by an intensity of the first light beam 12.

Step 150: estimating a first optional property.

In step 150, it is sought to estimate a first optical property $p_1$ of the sample, for example the absorption coefficient $\mu_a(\lambda)$, in the spectral band $\lambda$ of the first light beam 12.

To achieve this, a model of the reflectance of the sample in the spectral band in question is used, this model taking account of a plurality of optical properties p, including the absorption coefficient $\mu_a$ and the reduced scattering coefficient $\mu'_s$. Models are produced by varying the absorption coefficient and the reduced scattering coefficient between a minimum value and a maximum value, respectively. A modelled reflectance $R_{(\mu_a,\mu'_s)}{}^{model}(\lambda)$ is thus obtained for each value of $\mu_a$ and of $\mu'_s$ in question. The modelling may be carried out on the basis of an analytical model or by using a stochastic method of Monte Carlo type.

A comparison may be drawn, for example in the form of a quadratic disparity between the measured reflectance $R(\lambda)$ and each modelled reflectance $R_{(\mu_a,\mu'_s)}{}^{model}(\lambda)$ according to the expression:

$$\Delta(\mu_a(\lambda), \mu'_s(\lambda)) = \sqrt{\left(R(\lambda) - R^{model}_{(\mu_a,\mu'_s)}(\lambda)\right)^2} \quad (5)$$

$$\text{where } (\mu_a(\lambda), \mu'_s(\lambda)) = \underset{\mu_a(\lambda),\mu'_s(\lambda)}{\operatorname{argmin}} \left( \sqrt{\left(R(\lambda) - R^{model}_{(\mu_a,\mu'_s)}(\lambda)\right)^2} \right). \quad (5')$$

Figure 3B:
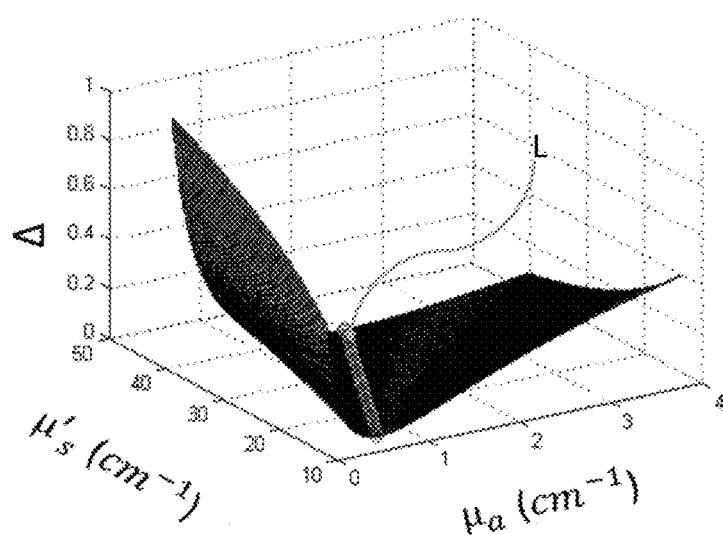
FIG. 3B shows a comparison between a first quantity of interest, measured using the configuration shown in FIG. 1A, and models of the first quantity of interest, each model being produced on the basis of an absorption coefficient and a reduced scattering coefficient of the sample.

FIG. 3B shows such a comparison $\Delta(\mu_a(\lambda), \mu'_s(\lambda))$ as a function of $\mu_a(\lambda)$ and $\mu'_s(\lambda)$ on the basis of an image measured on a test sample in a spectral band centred on 600 nm. The optical properties $(\mu_a(\lambda), \mu'_s(\lambda))$ of the sample are those that minimize the difference $\Delta(\mu_a(\lambda), \mu'_s(\lambda))$. However, this difference does not take a minimum value for one point in space $(\mu_a(\lambda), \mu'_s(\lambda))$, but rather across a multitude of points, forming a line L. Thus, the problem is indeterminate, since it does not have one solution, i.e. a pair $(\mu_a(\lambda), \mu'_s(\lambda))$ but rather a plurality, or even an infinity, of solutions. In order to estimate one of these two optical properties, for example $\mu_a(\lambda)$, the value of the other optical property, in this instance $\mu'_s(\lambda)$, has to be established beforehand.

According to the prior art, in order to correct this uncertainty, a predetermined value of the reduced scattering coefficient $\mu'_s$ is considered. In publication Bjorgan 2014, the coefficient $\mu'_s$ is set according to an analytical scattering model, based on samples that are considered to be representative of the sample under analysis.

The inventors have demonstrated that such an approach leads to a potentially critical measurement error, as described below in conjunction with FIGS. 4A and 4B. They have concluded that in order to remove this uncertainty, it is preferable, instead of using a predetermined value of the reduced scattering coefficient, that is supposed to be representative of the sample under examination, to measure this value directly on the sample under examination.

To achieve this, a second modality is used, the aim of which is to estimate, at least locally, an auxiliary optical property of the sample 5, in this instance the reduced scattering coefficient $\mu'_s$.

Stated otherwise, the proposed method aims to estimate a first optical property of the sample, for example $\mu_a$, in one spectral band, using a first modality, this estimate being based on a measurement of an auxiliary optical property of the sample, for example $\mu'_s$, in the spectral band, by means of a second measurement modality that is independent of the first modality.

In this example, the auxiliary optical property is measured by means of a DRS method, the aim of which is to form an elementary illumination zone 23 on the surface 5s of the sample 5 and to detect at least one scattered radiation, and preferably at least two radiations $24_1, 24_2, 24_3$ backscattered over two backscattering distances $D_1, D_2, D_3$ which are non-zero and differ from one another. This method is applied locally, to at least one element of the surface 5i of the surface 5s, as shown in FIG. 1B. The implemented device may be that described in conjunction with FIG. 1B, and applied according to the method described in publication "Sorgato 2015", the main steps of which are as follows:

Step 200: Illumination

In this step, the sample is illuminated by activating the auxiliary light source 20 so as to direct an auxiliary light beam, or second light beam 22, onto the surface 5s of the sample 5, the intersection of the auxiliary light beam 22 with the surface 5s of the sample forming an elementary illumination zone 23. The light source may be for example a tungsten halogen lamp with reference HL 2000 from Ocean Optics.

Step 210: Detection of signals backscattered over various backscattering distances.

In this step, the auxiliary photodetector 28 detects at least two signals $24_1, 24_2$ backscattered over two different backscattering distances $D_1, D_2$. In this example, the auxiliary photodetector 28 is a spectrometer such as the MAYA2000 Pro from Ocean Optics. At each backscattering distance $D_n$, a detected signal, referred to as the backscattering signal $S_n(\lambda)$, is formed in the spectral band $\lambda$, the index n denoting the backscattering distance. Each backscattering signal $S_n(\lambda)$ is preferably corrected from a dark signal $S_{black}$, measured in the dark over one and the same duration of acquisition, the auxiliary light source being switched off. The dark signal $S_{black}$ is representative of the noise of the auxiliary photodetector 28 and of a level of darkness in which the sample is placed.

Alternatively, the sample may be illuminated in succession by the auxiliary light source 20 in various spectral bands $\lambda$, the auxiliary photodetector 28 not being spectrally resolved. It may in particular be an image sensor, as described in conjunction with FIGS. 5A to 5C.

Step 220: Normalization and application of corrective factors in order to obtain an auxiliary quantity of interest, or second quantity of interest.

In this step, each detected backscattering signal $S_n(\lambda)$, corrected by the dark signal $S_{black}$, is normalized by a duration of acquisition $\delta t$ and by a quantity of light $S_{source}(\lambda)$ emitted by the auxiliary light source 20. Such a quantity of light may be measured by positioning an optical fibre, referred to as the excitation return optical fibre 21e, between the auxiliary light source 20 and the auxiliary photodetector 28.

A calibration factor, referred to as the second calibration factor $f_n(\lambda)$, is also applied to each backscattering signal $S_n(\lambda)$ thus corrected and normalized. This second calibration factor, dependent on the backscattering distance $D_n$, takes account of the effect of various components of the illumination fibre 21 and of the detection fibre $27_n$ on the backscattering signal. In a manner analogous to the first calibration factor f ($\lambda$) described in step 140, each second calibration factor is determined in a calibration phase, implementing a calibration sample the optical properties of which are known. This calibration factor corresponds to a ratio of a modelled reflectance $R_{calib,n}^{model}(\lambda)$ of the calibration sample at the backscattering distance $D_n$ to a reflectance $R_{calib,n}(\lambda)$ of the calibration sample measured by the device, at the same wavelength and at the same backscattering distance, while keeping the same experimental parameters as with the sample under analysis: the same adjustments to the source 20 and to the photodetector 28, the same distance from the calibration sample with respect to the source and to the photodetector.

The second calibration factor is such that $$f_n(\lambda) = \frac{R_{calib,n}^{model}(\lambda)}{R_{calib,n}(\lambda)} \quad (6)$$

$$\text{where: } R_{calib,n}(\lambda) = \frac{S_{calib,n}(\lambda) - S_{black}(\lambda)}{S_{source}(\lambda) \times \delta t_{calib}}, \quad (6')$$

$S_{calib,n}(\lambda)$ denoting the backscattering signal, at a backscattering distance $D_n$, measured by the auxiliary photodetector 28 when the measured sample is the calibration sample, $\delta t_{calib}$ denoting the duration of acquisition of the backscattering signal $S_{calib,n}(\lambda)$.

Furthermore, certain parameters of the device may vary between the time $t_0$ at which the calibration described above was carried out and the time t of measurement. It may for example take account of a variation in the sensitivity of the auxiliary photodetector 28 or the ageing of the detection optical fibres 27.

In order to take account of this variability, a correction factor, referred to as the second correction factor, $k_n(\lambda)$ may be applied, such that $$k_n(\lambda) = \frac{f_{t,n}(\lambda)}{f_{t0,n}(\lambda)}, \quad (7)$$

where $f_{t,n}(\lambda)$ and $f_{t0,n}(\lambda)$ represent calibration factors measured at times t and $t_0$, respectively.

This step allows a reflectance of the sample $R_n(\lambda)$, at the backscattering distance $D_n$ and at the wavelength $\lambda$, to be obtained according to the expression:

$$R_n(\lambda) = \frac{S_n(\lambda) - S_{block}(\lambda)}{S_{source}(\lambda) \times \delta t} \times f_n(\lambda) \times k_n(\lambda). \quad (8)$$

This reflectance corresponds to an auxiliary quantity of interest, representative of an intensity of radiation backscattered at a non-zero backscattering distance $D_n$ with respect to the elementary illumination zone 23. This backscattered radiation may also be referred to as the "second backscattered radiation".

Step 230: Determining the local optical properties of the sample

For at least one wavelength $\lambda$, and considering at least as many different backscattering distances $D_n$ as there are optical properties to estimate, the optical properties p having the least disparity between the reflectance $R_n(\lambda)$, determined in step 220 at wavelength $\lambda$, and a modelled reflectance $R_{n,p}^{model}(\lambda)$ are determined, this reflectance $R_{n,p}^{model}(\lambda)$ being modelled by considering a plurality of values of the optical properties p at the backscattering distance $D_n$. This determination may be carried out by minimizing a quadratic disparity, and for example according to the expression:

$$p = \underset{p}{\mathrm{argmin}} \left( \sum_{n=1}^{N} (R_{n,p}^{model}(\lambda) - R_n(\lambda))^2 \right) \quad (9)$$

N denotes the number of backscattering distances taken into account;

$R_{n,p}^{model}$ is a reflectance modelled, at the backscattering distance $D_n$, by taking account of at least one optical property p. The parameter p may correspond to one optical property or to a set of optical properties.

In this example, the optical properties sought are $\mu_a(\lambda)$ and $\mu'_s(\lambda)$. Thus, the pair $(\mu_a(\lambda), \mu'_s(\lambda))$ sought is that having the least disparity between the reflectance $R_n(\lambda)$ measured at wavelength $\lambda$ and a reflectance $R_{n,\mu a,\mu s}^{model}(\lambda)$ modelled $\lambda$ for various values of $\mu_a(\lambda)$ and of $\mu'_s(\lambda)$ at the backscattering distance $D_n$. This may be determined according to the expression:

$$(\mu_a(\lambda), \mu'_s(\lambda)) = \underset{\mu_a(\lambda),\mu'_s(\lambda)}{\mathrm{argmin}} \left( \sum_{n=1}^{N} (R_{n,\mu a,\mu s}^{model}(\lambda) - R_n(\lambda))^2 \right), \quad (9')$$

$R_{n,\mu a,\mu s}^{model}(\lambda)$ denoting a reflectance modelled, at the backscattering distance $D_n$, by considering various values of $\mu_a(\lambda)$ and $\mu'_s(\lambda)$.

The various modelled reflectance values $R_{n,\mu a,\mu s}^{model}(\lambda)$ are obtained for a plurality of pairs of values $\mu_a(\lambda)$, $\mu'_s(\lambda)$ in a parameter-setting phase by means of numerical simulation implementing a method of Monte Carlo type or by means of analytical modelling.

Step 240: transmission of the auxiliary optical property or reiteration.

In this step, the auxiliary optical property, in this instance the reduced scattering coefficient $\mu'_s(\lambda)$, determined in step 230, is transmitted in order to be used for calculating the first optical property. The optical properties determined in step 230 may also be used for selecting a second calibration factor, used in another iteration of step 220, as described below.

Preferably, in step 220, a plurality of second calibration factors $f_n(\lambda)$ are available, produced using calibration samples the optical properties p of which, in particular $\mu_a(\lambda)$ and/or $\mu'_s(\lambda)$, differ. It is also possible to calculate calibration factors by interpolation between two calibration factors obtained using two respective calibration samples having different optical properties. Second calibration factors, denoted by $f_n^p(\lambda)$, are then available, which factors are associated with each backscattering distance $D_n$ and with various values of the optical properties p. In a first iteration of step 220, a second calibration factor $f_n^p(\lambda)$, corresponding to arbitrarily defined optical properties, is used. Subsequent to step 240, step 220 may be reiterated, by taking account of a second calibration factor $f_n^p(\lambda)$ corresponding to the optical properties p determined in step 230. The method may be reiterated multiple times, but the inventors estimate that two iterations are generally sufficient. The second correction factor $k_n$ may be determined only on a single calibration sample and used regardless of which second calibration factor $f_n^p(\lambda)$ is applied. The adaptation of the second calibration factor to optical properties of the sample determined in a preceding iteration, which method is referred to as the adaptive calibration factor method, is described in publication Sorgato 2015. This makes it possible to limit measurement errors due to taking account of a calibration factor that is not representative of the actual optical properties of the sample under examination.

Thus, step 230 allows an auxiliary optical property relating to scattering, in this instance $\mu'_s(\lambda)$, to be locally measured, this property being used in step 150 to estimate the first optical property, in this instance $\mu'_a(\lambda)$, using the first modality. It is preferable for the spectral band $\lambda$, at which the auxiliary optical property is measured, to be close to or included within the spectral band $\lambda$ at which the first optical property is estimated. Measuring the auxiliary optical property $\mu'_s(\lambda)$ makes it possible to remove the uncertainty mentioned in conjunction with step 150 and to estimate, in this step, the value $\mu_a(\lambda)$ that minimizes the disparity function $\Delta(\mu_a, \mu'_s)$ mentioned in conjunction with equation (5).

Steps 100 to 150 are preferably implemented for various zones of interest ROI in the first image, thereby making it possible to estimate the first optical property at each of these zones of interest. An estimate of the first optical property at various points on the surface of the sample is then obtained. A region of interest may corresponds to one pixel or to a group of pixels of the first image. A group of pixels may be composed of pixels of the same intensity or of intensities located within one and the same range of values. A group of pixels may also result from an arbitrary meshing of the surface of the sample at various regions of interest ROI.

Figure 3C:
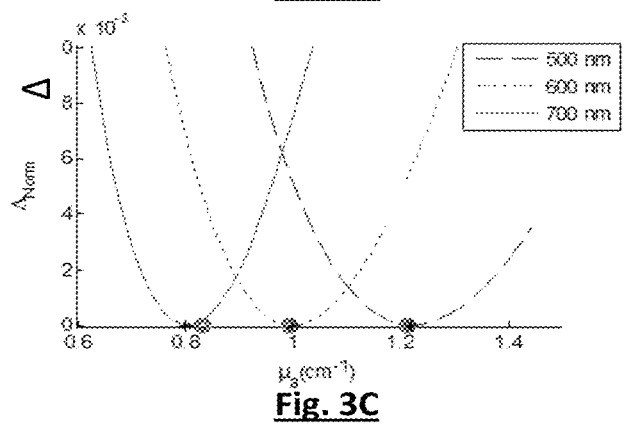
FIG. 3C shows absorption coefficients of a sample that are determined by implementing the steps described in conjunction with FIG. 2 at three different wavelengths.

FIG. 3C illustrates disparity functions $\Delta(\mu_a(\lambda), \mu'_s(\lambda))$ such as given in equation (5), obtained using a first test sample IL1-1.5% at three wavelengths: $\lambda=500$ nm, $\lambda=600$ nm and $\lambda=700$ nm, the coefficient $\mu'_s(\lambda)$ of the test sample having been measured at these three wavelengths. The first test sample IL1-1.5% is a sample including a concentration of India ink allowing an absorption coefficient $\mu_a(\lambda)$ equal to 1 cm$^{-1}$ at $\lambda=600$ nm to be obtained, and including a concentration by volume of Intralipid of 1.5%. This disparity function includes only one unknown, namely $\mu_a(\lambda)$. For each wavelength, the value $\mu_a(\lambda)$ minimizing the disparity function is the absorption coefficient of the sample. FIG. 3C shows the estimated values, represented by a circle, these being close to the actual values, represented by an asterisk *.

In the above, an absorption property $\mu_a(\lambda)$ (first optical property) is estimated using the multispectral imaging modality (MSI—1$^{st}$ modality), while a backscattering property $\mu'_s(\lambda)$ (auxiliary optical property) is estimated using diffuse reflectance spectrometry (DRS—2$^{nd}$ modality) applied to the sample. Alternatively, a scattering property $\mu'_s(\lambda)$ (first optical property) could be estimated by means of multispectral imaging and an absorption property $\mu_a(\lambda)$ (auxiliary optical property) could be measured by means of diffuse reflectance spectrometry. However, the depth of field of DRS is greater for the measurement of a scattering coefficient than for the measurement of an absorption coefficient, this depth of field being around 2 mm for the measurement of $\mu'_s(\lambda)$ and around 500 µm for the measurement of $\mu_a(\lambda)$, using the DRS measurement device described above. Thus, the measurement of an absorption coefficient by DRS assumes a particularly precise focusing of the device shown in FIG. 1B. This focusing constraint is less severe when DRS is used to determine a scattering coefficient $\mu'_s(\lambda)$. Furthermore, the depth of field of multispectral imaging, applied in the determination of $\mu_a(\lambda)$, is greater than the depth of field of DRS, using the device described above. For these reasons related to the depth of field, It is preferable to use DRS to measure a scattering optical property $\mu'_s(\lambda)$ and to use MSI to measure an absorption optical property $\mu_a(\lambda)$.

Furthermore, regardless of the embodiment, the first optical property estimated by means of the first modality at various regions of interest on the sample may be reset in at least one region of interest using a first auxiliary optical property measured by means of the second modality.

The advantage of multispectral imaging is that an estimate of the first optical property of the sample is obtained at various zones of interest ROI in the first image $I_1(\lambda)$, each region of interest ROI being defined by a pixel or a plurality of pixels (x, y) of the first image. Thus, when the first optical property is an absorption coefficient, a spatial distribution $\mu_{a-x,y}(\lambda)$ of the absorption coefficient on the surface 5s of the sample is obtained. The second modality allows an auxiliary optical property of the sample, for example a reduced scattering coefficient $\mu'_s(\lambda)$ to be measured at one or more surface elements 5, of the sample, as described below, in particular in conjunction with FIGS. 5B and 5C.

According to one variant, upon completion of step 150, step 140 may be reiterated using, in expression (4), a first calibration factor taking account of the first optical property resulting from step 150 for the region of interest in question, and potentially of the auxiliary optical property. Such a calibration factor may be obtained from a calibration sample the first optical property of which corresponds to the first optical property resulting from step 150, or by interpolation between calibration factors obtained from various respective samples, the aim of the interpolation being to estimate a calibration factor corresponding to the first optical property estimated beforehand and/or the auxiliary optical property measured on the sample. Steps 150 and 140 may thus be reiterated until a convergence criterion is reached, for example a predetermined number of iterations or a small disparity between two first optical properties estimated in two respective successive iterations. Stated otherwise, in this variant, in the first modality, a first adapted calibration factor is applied to the first optical property of the sample, and potentially to the auxiliary optical property of the sample. This allows a better estimate of the first optical property to be obtained. It should be specified that such an iterative process does not require measurement of the auxiliary optical property but may be based on an estimate thereof, but it is still preferable to measure the auxiliary optical property on the sample under examination.

The inventors compared the estimates of the absorption coefficient $\mu_a(\lambda)$ using multispectral imaging, by considering either an arbitrary value of a reduced scattering coefficient, as in the prior art, or a value of this coefficient measured by means of DRS, on the sample under examination. These estimates were made at three wavelengths, 500 nm, 600 nm and 700 nm, respectively.

Figure 4A:
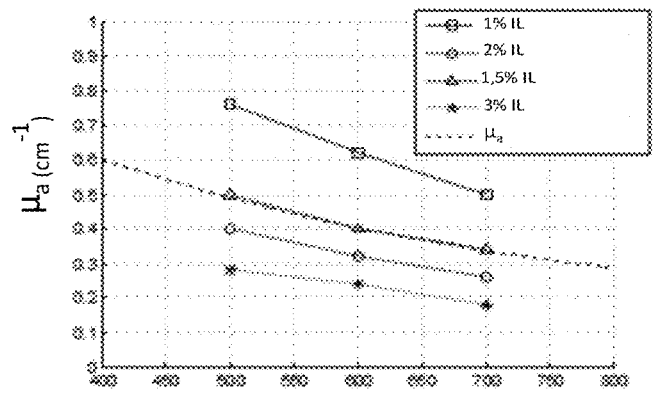
FIG. 4A shows estimates, at various wavelengths, of the absorption coefficient of four test samples, based on a reduced scattering coefficient being arbitrarily taken into account.

FIG. 4A shows the $\mu_a(\lambda)$ estimates of the four test samples 1% IL, 1.5% IL, 2% IL and 3% IL, the concentration by volume of Intralipid of which is 1%, 1.5%, 2% and 3%, respectively. These test samples have one and the same absorption coefficient $\mu_a(\lambda)$, this being represented by a dotted line in FIGS. 4A and 4C. Its value is 0.4 cm$^{-1}$ at 600 nm. Each sample has its own reduced scattering coefficient, such that the percentage of Intralipid corresponds to a value of a reduced scattering coefficient. These estimates are made on the basis of images of each test sample, such as shown in FIG. 3A. In this figure, regions of interest are shown with an identifying percentage, each region of interest corresponding to a test sample. Each region of interest has been processed by considering one measurement of the reduced scattering coefficient $\mu'_s(\lambda)$ taken on the test sample 1.5% IL, this sample being, in this example, taken as representative of the other test samples. It may be seen that only the estimate of the absorption coefficient $\mu_a(\lambda)$ of the sample 1.5% IL is reliable. The estimates linked to the other samples are assigned a substantial measurement error even though they are based on the reduced scattering coefficient $\mu'_s(\lambda)$ of the test sample 1.5% IL, the compositions of which are nonetheless close to those of the other test samples.

Figure 4B:
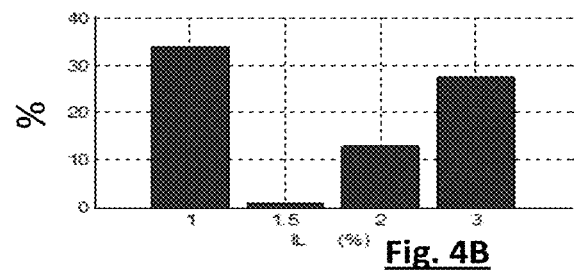
FIG. 4B illustrates the measurement errors associated with the estimates presented in FIG. 4A.

FIG. 4B illustrates the mean relative error of the estimates of the absorption coefficient $\mu_a(\lambda)$ at the three wavelengths shown in FIG. 4A, for each test sample. Only the estimate relating to the sample 1.5% IL is satisfactory.

Figure 4C:
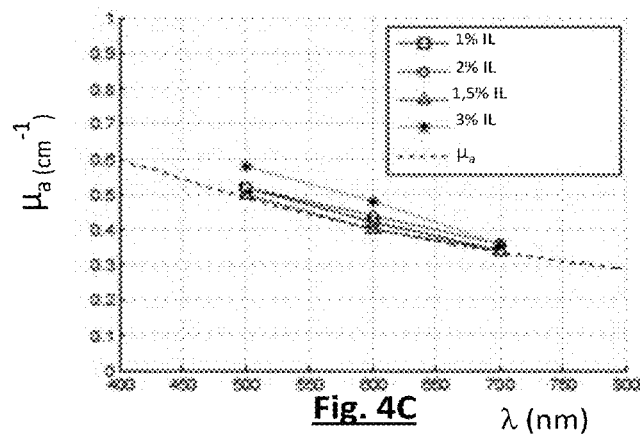
FIG. 4C shows estimates, at various wavelengths, of the absorption coefficient of four test samples, based on a measurement of a reduced scattering coefficient taken on each sample.

In order to obtain a reliable estimate of the absorption coefficient, it is necessary to use a measurement of the reduced scattering coefficient $\mu'_s(\lambda)$ on the sample under examination, rather than other estimates, as the basis, even when these other estimates are obtained on the basis of samples the compositions of which are close to those of the sample under examination. FIG. 4C shows the estimates of $\mu_a(\lambda)$ obtained on each test sample 1% IL, 1.5% IL, 2% IL and 3% IL by considering four different values of the reduced scattering coefficient $\mu'_s(\lambda)$, these values having been measured on each of these test samples, respectively. The reduced scattering coefficient $\mu'_s(\lambda)$ of each test sample was estimated by means of DRS at the three wavelengths mentioned above. The absorption coefficient $\mu_a(\lambda)$ of each test sample is subsequently estimated by means of multispectral imaging, taking account of the reduced scattering coefficient measured on each thereof. It is observed that the estimated values of $\mu_a(\lambda)$ are substantially closer to the actual value.

Figure 4D:
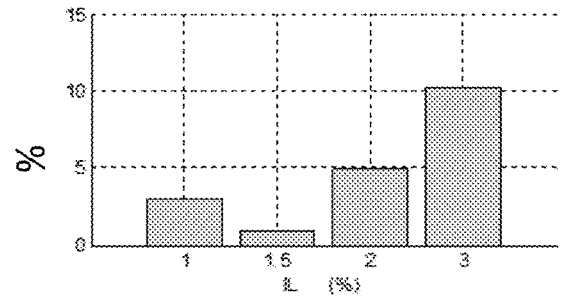
FIG. 4D illustrates the measurement errors associated with the estimates presented in FIG. 4C.

FIG. 4D illustrates the mean error in the estimate of the absorption coefficient $\mu_a(\lambda)$ at the three wavelengths. It is observed that these errors are smaller than those shown in FIG. 4B. The measurement of the absorption coefficient $\mu_a(\lambda)$ of a sample, based on a measurement of the reduced scattering coefficient $\mu_s'(\lambda)$ measured on each sample, is therefore more reliable.

The inventors have made another series of measurements by iteratively measuring the auxiliary optical property, i.e. the reduced scattering coefficient, the second calibration factor taking account of said coefficient measured in a preceding iteration. This method of adapting the calibration factor, described above, allows the second calibration factor to be adapted to the optical properties of the sample, and results in a better estimate of the reduced scattering coefficient. Consequently, the error in the measurement of the first optical property, i.e. the absorption coefficient, is systematically less than 5%. The precision of the measurement is therefore enhanced.

One of the key points in the approach proposed by the inventors is the local measurement of an auxiliary optical property in order to provide a better estimate of a first optical property on the basis of the first image $I_1(\lambda)$. The auxiliary optical property it is estimated in a pointlike manner, at a surface element $5i$ of the surface $5s$ of the sample. The location of this surface element $5i$ may be determined on the basis of the first image $I_1(\lambda)$. This first image may for example be segmented into zones having pixels $I_{1(x,y)}$ of the same, or comparable, intensity, the auxiliary optical property being estimated on one or more zones arising from this segmentation. Thus, the first image $I_1(\lambda)$ may make it possible to define the location of the surface element $5i$, or a mesh of surface elements $5i$, on which the auxiliary optical property is measured. The auxiliary optical property may be measured successively on each surface element thus defined by applying steps 200 to 240 described above, the device shown in FIG. 1B scanning the surface of the sample.

According to one variant, the surface elements $5i$ are determined arbitrarily, for example in the form of a regular or irregular mesh set up on the surface of the sample. The auxiliary optical property is then measured at each point in this mesh.

The application of the second measurement modality to various surface elements $5i$ makes it possible to discretely measure the auxiliary optical property for each surface element distributed discretely in a mesh on the surface of the sample. It is then possible to interpolate the various measurements, so as to estimate the auxiliary optical property between each section of the mesh. The interpolation may be linear or polynomial. Thus, the first optical property, at a region of interest ROI in the first image $I_1(\lambda)$, may be determined on the basis of an auxiliary optical property, either measured at this region of interest when this region coincides with a surface element $5i$ or interpolated on the basis of auxiliary optical properties measured at various respective surface elements of the sample, in particular those adjacent to the region of interest ROI.

Figure 5A:
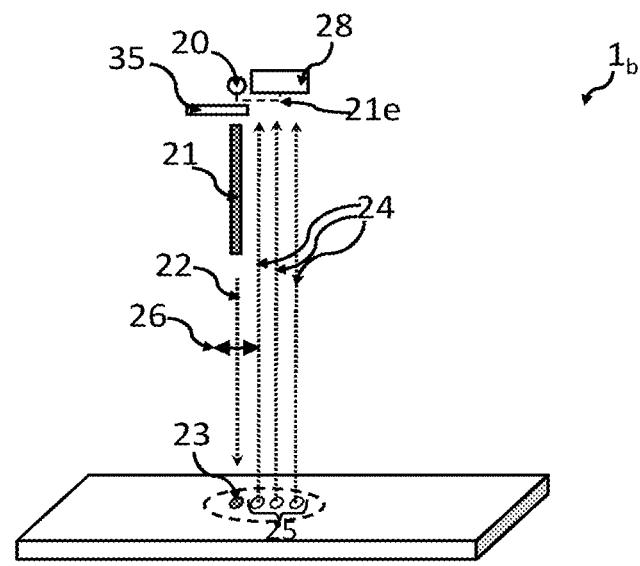
FIG. 5A shows one embodiment of the second component of a device according to the invention.
Figure 5B:
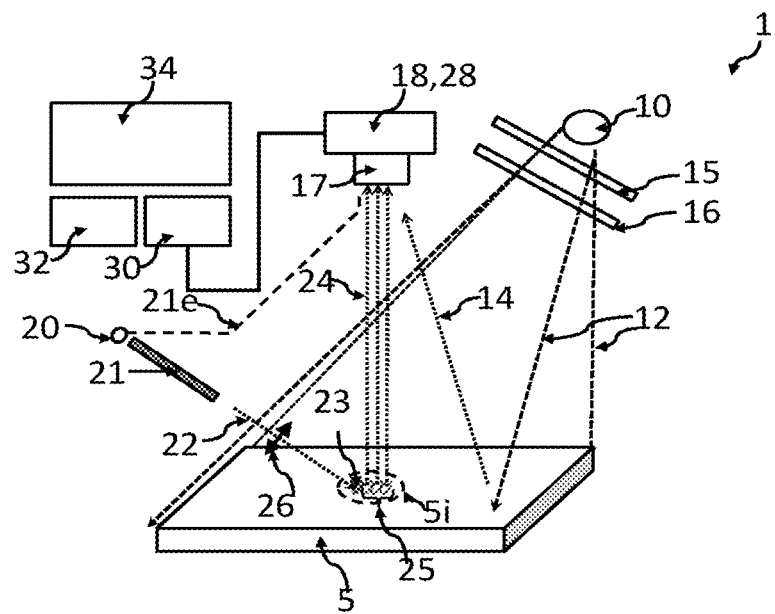

FIGS. 5A to 5C show variants of the device 1. FIG. 5A shows the second component 1b allowing DRS measurements to be taken. In this figure, with respect to FIG. 1B, the detection optical fibres 27 and the optical switch 29 have been omitted. The auxiliary photodetector 28 is an auxiliary image sensor, or second image sensor. In this configuration, the auxiliary photodetector is not spectrally resolved, it being possible to modulate the spectral band of the auxiliary light beam 22. The auxiliary light source 20 may be combined with optical filters, for example in the form of a filter wheel 35. Alternatively, the auxiliary light source includes elementary light sources, for example laser diodes or light-emitting diodes, emitting in various spectral bands. The auxiliary image sensor 28 is optically coupled to the surface $5s$ of the sample, such that the elementary backscattering zones 25 are separate from one another and separate from the elementary illumination zone 23. The auxiliary light source may be a collimated auxiliary light beam forming the illumination zone 23, in which case the illumination optical fibre 21 and its optical system 26 may be omitted. As in FIG. 1B, an excitation return fibre $21e$ may guide the emitted auxiliary light beam 22 towards the auxiliary photodetector 28.

FIG. 5B shows a device 1 including the first and second components 1a and 1b. In this device, the first image sensor 18 and the auxiliary image sensor 28 are combined and form one and the same image sensor, making it possible to acquire:
- a first image $I_1(\lambda)$ of the sample 5 when this sample is illuminated by a first light beam 12, this beam covering an extended area of the sample;
- a second image $I_2(\lambda)$ of the sample 5 when this sample is illuminated by an auxiliary light beam 22, this beam forming an elementary illumination zone 23 on the surface of the sample.

The first beam 12 and the auxiliary beam 12, 22 are emitted by the first light source 10 and by the auxiliary light source 20, respectively, in one spectral band, and potentially in various spectral bands in succession. The optical system 17 may be adjusted between the acquisition of the first image and of the second image. As in FIGS. 1B and 5A, an excitation return fibre 21e may guide the emitted auxiliary light beam 22 towards the auxiliary photodetector 28.

The first image $I_1(\lambda)$ is processed by the microprocessor 30, so as to estimate a first optical property, in steps 100 to 150 described above. The second image $I_2(\lambda)$ is processed by the microprocessor 30 so as to determine, in this image, the intensity of signals $S_n(\lambda)$ backscattered at various backscattering distances $D_n$ followed by the implementation of the method described in conjunction with steps 200 to 240 for measuring an auxiliary optical property of the sample, this property being used, in step 150, to estimate the first optical property.

In the embodiments described above, the first image $I_1(\lambda)$ makes it possible to estimate an optical property on the basis of various regions of interest ROI in the first image, each region of interest corresponding to a pixel $I_{1,xy}(\lambda)$, or a group of pixels, of the image. The second modality makes it possible to make a pointlike estimate, i.e. at a surface element 5i, of the auxiliary optical property. The auxiliary light beam 22 may be directed onto various surface elements 5i in succession, so as to make successive estimates of the auxiliary optical property of the sample at each surface element 5i.

The embodiment shown in FIG. 5C makes it possible to simultaneously form various elementary illumination zones 23 which are distributed over the surface of the sample. To achieve this, a mask 36 is positioned between the auxiliary light source 20 and the surface of the sample 5. Such a mask consists of transparent portions $36_1$ and opaque portions $36_2$, these portions being projected onto the surface of the sample 5. FIG. 5D show an example of such a mask. As many elementary illumination zones $23_1$, $23_2$, $23_3$ as there are projected transparent portions are then obtained. An optical system 26 for focusing the auxiliary light beam 22 may be positioned on the surface of the sample. An excitation return optical fibre 21e may link the auxiliary light source 20 to the image sensor. The auxiliary image sensor 28, which is here combined with the first image sensor 18, forms a second image $I_2(\lambda)$ in which various elementary illumination zones 23, and the various elementary backscattering zones 25 associated with each elementary illumination zone, appear. Steps 200 to 240 are implemented on the basis of the intensity of the elementary backscattering zones 25 associated with one and the same elementary illumination zone 23. The auxiliary optical property is estimated, at various discrete locations 5i, on the basis of the same image $I_2(\lambda)$. This device avoids scanning the auxiliary light beam 20 over the surface of the sample, since the mask allows multiple auxiliary beams $22_1$, $22_2$, $22_3$ etc. to be formed simultaneously. The mask may consist of a regular arrangement of opaque portions and transparent portions. It may be a glass plate or grid on which an opaque pattern has been formed. It may also be a liquid crystal screen, thereby making it possible to form a mask the opaque pattern of which can be modulated.

FIG. 6 schematically shows one embodiment of the invention, applied to the surface of a sample. A first image $I_1(\lambda)$ is formed, on the basis of which surface elements are determined on which the auxiliary optical property, in this instance the reduced scattering coefficient, is discretely measured. The interpolation of the measurements makes it possible to obtain a spatial distribution $\mu'_{s,xy}(\lambda)$ of the auxiliary optical property $\mu_s'(\lambda)$. This spatial distribution is used to estimate the absorption coefficient $\mu_a(\lambda)$ and to obtain a spatial distribution $\mu_{a,xy}(\lambda)$ thereof. A quantitative estimate of the spatial distribution of the optical properties relating to absorption and to scattering on the surface of the sample under examination is then available.

The method and the device that are the subject matter of the invention could be implemented on biological samples, for example biological tissues, for the purpose of assisting with diagnosis, in particular in the case of skin diseases. It may also be implemented in monitoring the vascularization of the skin, for example following grafts, or in the analysis of skin samples taken during an operation, in particular for the purpose of delimiting tumourous areas with respect to healthy areas.

Besides biological samples, the method could be implemented for the purpose of monitoring samples, for example in the food and agriculture industry or in environmental monitoring.

The invention claimed is:

1. A method for estimating optical properties of a sample, comprising the following steps:
   a) illuminating a surface of the sample using a first light beam, produced by a first light source;
   b) acquiring, using a first image sensor, a first image of light radiation backscattered by the sample thus illuminated;
   c) using the first image, determining, at multiple regions of interest on the surface of the sample, a first quantity of interest, representative of a quantity of the light radiation backscattered by the sample; and
   d) estimating a first optical property at each of the regions of interest, using the first quantity of interest,
   the method further comprising, prior to step d):
      determining at least one surface element of the sample on the basis of the first image acquired in step b); and
      measuring an auxiliary optical property of the sample that differs from the first optical property, the auxiliary optical property of the sample being measured according to each of said at least one surface element thus determined,
      such that each estimate made in step d) takes account of the auxiliary optical property thus measured on the sample.

2. The method according to claim 1, wherein:
   either the first optical property is a light absorption property of the sample, the auxiliary optical property being a light scattering property of the sample,
   or the first optical property is a light scattering property of the sample, the auxiliary optical property being a light absorption property of the sample.

3. The method according to claim 1, wherein the step of measuring the auxiliary optical property comprises the following sub-steps:
   i) illuminating the surface of the sample using an auxiliary light beam, produced by an auxiliary light source, so as to form, on the surface of the sample, an elementary illumination zone, corresponding to a portion of the surface illuminated by the auxiliary light beam;
ii) measuring, using an auxiliary photodetector, a backscattering signal, representative of radiation backscattered by the sample, the backscattered radiation emanating from an elementary backscattering zone, separated from the elementary illumination zone and located at a distance, referred to as the backscattering distance, from the latter; and
iii) estimating the auxiliary optical property of the sample on the basis of the backscattering signal measured in sub-step ii).

4. The method according to claim 3, wherein:
sub-step ii) includes obtaining, on the basis of the backscattering signal, a quantity of interest, referred to as the auxiliary quantity of interest, representative of a quantity of the radiation backscattered by the sample, at a backscattering distance, subsequent to the illuminating by the auxiliary light beam, and
sub-step iii) includes comparing the auxiliary quantity of interest with a plurality of estimates of this quantity of interest, each estimate being made by considering a predetermined value of the auxiliary quantity of interest.

5. The method according to claim 3, wherein:
in sub-step i), the sample is successively or simultaneously illuminated by a plurality of auxiliary light beams so as to form, on the surface of the sample, a plurality of elementary illumination zones that are spaced apart from one another, and
sub-steps ii) and iii) are implemented by considering a backscattered signal emitted at a backscattering distance from each elementary illumination zone, so as to estimate the auxiliary optical property in as many surface elements as there are auxiliary light beams.

6. The method according to claim 1, wherein step d) comprises, in each region of interest, comparing the first quantity of interest determined in step c) with a plurality of estimates of this quantity of interest, each estimate being made by considering a predetermined value of the first optical property and by taking account of the auxiliary optical property previously measured on the sample.

7. The method according to claim 1, wherein the auxiliary optical property of the sample is measured at a plurality of surface elements of the sample.

8. The method according to claim 7, comprising interpolating the auxiliary optical property on the basis of at least two auxiliary optical properties measured beforehand, so as to establish a spatial distribution of the auxiliary optical property.

9. A device for estimating optical properties of a sample comprising:
a first light source configured to emit a first light beam that is propagated towards the sample;
a first image sensor configured to acquire a first image of a first light radiation backscattered by the sample;
an auxiliary light source configured to emit an auxiliary light beam that is propagated towards the sample, so as to form, on a surface of the sample, an elementary illumination zone, corresponding to a portion of a surface of the sample that is illuminated by the auxiliary light beam;
an auxiliary photodetector configured to measure a radiation backscattered by the sample, at a backscattering distance from the elementary illumination zone, subsequent to the illumination of the sample by the auxiliary light source; and
a microprocessor, configured to determine an auxiliary optical property of the sample on the basis of the backscattered radiation measured by the auxiliary photodetector, the microprocessor also being configured to determine a first optical property differing from the auxiliary optical property, at various points on the surface of the sample, each point being determined on the basis of the first image acquired by the first image sensor, the first optical property being determined by taking account of the auxiliary optical property.

10. The device according to claim 9, wherein the auxiliary photodetector is an image sensor.

11. The device according to claim 9, wherein the auxiliary photodetector is the first image sensor.

12. The device according to claim 9, wherein the auxiliary light source is further configured to simultaneously form a plurality of elementary illumination zones, spaced apart from one another, on the surface of the sample.

13. The device according to claim 12, further comprising a mask, interposed between the auxiliary light source and the sample, the mask comprising transparent portions, allowing the auxiliary light beam to pass through, and opaque portions, blocking the auxiliary light beam, such that each elementary illumination zone is formed by a projection of a transparent portion onto the surface of the sample.

14. The device according to claim 13, wherein the microprocessor is further configured to:
using the first image, determine, at multiple regions of interest on the surface of the sample, a first quantity of interest, representative of a quantity of the light radiation backscattered by the sample; and
estimate a first optical property at each of the regions of interest, using the first quantity of interest.

* * * * *